(12) United States Patent
Belef et al.

(10) Patent No.: US 7,686,816 B2
(45) Date of Patent: *Mar. 30, 2010

(54) DRIVEABLE CATHETER SYSTEMS AND METHODS

(75) Inventors: W. Martin Belef, San Jose, CA (US); John H. Ream, San Jose, CA (US); Thomas C. Moore, Fremont, CA (US); Steven N. Roe, San Mateo, CA (US); Jeffrey M. Jones, Sunnyvale, CA (US); Niyazi Beyhan, Santa Clara, CA (US); Arcadi Elbert, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/254,234

(22) Filed: Oct. 18, 2005

(65) Prior Publication Data

US 2006/0084911 A1 Apr. 20, 2006

Related U.S. Application Data

(63) Continuation-in-part of application No. 09/167,178, filed on Oct. 6, 1998, now abandoned.

(51) Int. Cl.
*A61M 25/01* (2006.01)
*A61B 19/00* (2006.01)

(52) U.S. Cl. .............. 606/108; 606/130; 604/95.01; 604/163; 604/171; 604/528; 600/585

(58) Field of Classification Search ............... 604/156, 604/158, 159, 163, 164.08, 171, 174, 528, 604/95.01–95.05; 606/1, 108, 130; 607/122; 600/585
See application file for complete search history.

(56) References Cited

U.S. PATENT DOCUMENTS

| | | | | |
|---|---|---|---|---|
| 4,679,557 A | * | 7/1987 | Opie et al. | 606/108 |
| 5,361,768 A | * | 11/1994 | Webler et al. | 600/445 |
| 5,827,313 A | * | 10/1998 | Ream | 606/171 |
| 5,957,941 A | * | 9/1999 | Ream | 606/159 |
| 6,319,227 B1 | * | 11/2001 | Mansouri-Ruiz | 604/95.01 |
| 6,398,755 B1 | * | 6/2002 | Belef et al. | 604/95.01 |
| 6,974,465 B2 | * | 12/2005 | Belef et al. | 606/108 |

* cited by examiner

*Primary Examiner*—(Jackie) Tan-Uyen T. Ho
*Assistant Examiner*—Katherine M Dowe
(74) *Attorney, Agent, or Firm*—Darby & Darby P.C.; Patrick R. Turner (57) ABSTRACT

The system (2) includes a catheter drive unit (22) and a catheter (24) extending therefrom movably mounted to a catheter drive sled (26). The catheter drive unit rotates and translates the catheter core (34) within the catheter sheath (36). The sled has a serrated, conical drive unit interface (82), with a bag-piercing tip (86) mateable with a translator drive output (92) so that a sterile drape (112) enclosing the catheter drive unit is automatically pierced when the catheter drive unit is mounted to the sled. A control unit (6) is spaced apart from the catheter drive unit and provides power and commands to the catheter drive unit and receives information and data from the catheter drive unit. The rotator and translator drive motors (54, 90) are operated from both the control unit and the catheter drive unit. Both the control unit and catheter drive unit have translation displacement displays (10, 30).

22 Claims, 5 Drawing Sheets

DRIVEABLE CATHETER SYSTEMS AND METHODS

CROSS-REFERENCE TO RELATED APPLICATIONS

This is a Continuation-in-part of U.S. patent application Ser. No. 09/167,178, filed Oct. 6, 1998 now abandoned, entitled "Driveable Catheter System", the disclosure of which is incorporated by reference. This is also related to U.S. patent application Ser. No. 09/130,198, filed Aug. 5, 1998, entitled "Automatic/Manual Longitudinal Position Translator and Rotary Drive System for Catheters"; U.S. patent application Ser. No. 09/047,064, filed May 7, 1998, entitled "Combined Motor Drive and Automatic Longitudinal Position Translator for Ultrasonic Imaging System"; U.S. patent application Ser. No. 08/721,433 filed Sep. 27, 1996, entitled "Catheter System and Drive Assembly Thereof"; U.S. patent application Ser. No. 08/722,325 filed Sep. 27, 1996, entitled "Device for Controlled Longitudinal Movement of an Operative Element Within a Catheter Sheath and Method"; and U.S. Pat. No. 5,361,768, issued Nov. 8, 1994, entitled "Automated Longitudinal Position Translator for Ultrasonic Positioning Probes, and Method of Using Same".

BACKGROUND OF THE INVENTION

The present invention relates generally to catheters systems. In particular, the present invention is directed to a catheter system that provides for the controlled longitudinal movement of an elongate element—such as a rotatable catheter core with an operative element, for example an ultrasonic transducer or an optical fiber imaging device, at its distal end, or a drive cable with an atherectomy cutter at its distal end—housed within a sheath positioned within a patient.

Arteriosclerosis, also known as atherosclerosis, is a common human ailment arising from the deposition of fatty-like substances, referred to as atheromas or plaque, on the walls of blood vessels. Such deposits occur in both peripheral blood vessels which feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma, and other devices that are pushed or pulled along or through a deposit, such as atherectomy where a blade or cutting bit is used to sever and remove the atheroma, spark gap reduction in which an electrical spark burns through the plaque, laser angioplasty where laser energy is used to ablate at least a portion of the atheroma, and opening of vessels through the use of stents.

Two major difficulties in using such devices are maintaining a constant translational rate for the device and obtaining images of and information on the region of the blood vessel to be treated. Several imaging techniques have been proposed. Catheters incorporating mechanical rotation of ultrasonic transducers for imaging are disclosed in U.S. Pat. Nos. 4,794,931; 5,000,185; 5,049,130; and 5,024,234. These catheters scan in a plane normal to the catheter axis. Catheters employing phased array imaging systems are disclosed in U.S. Pat. Nos. 4,841,977 and 4,917,097. Catheters employing fiber optic imaging components are also known.

Generally deposits extend some longitudinal distance along the length of a vessel. To view different portions of the deposit a physician typically moves a handle attached to a proximal end of the imaging catheter along the vessel, for example, by pushing or pulling the catheter.

Imaging using computer-assisted reconstruction algorithms enables physicians to view a representation of the patient's interior intravascular structures in two or three dimensions (i.e., so-called three-dimensional or longitudinal view reconstruction). In this connection, image reconstruction algorithms typically employ data-averaging techniques which assume that the intravascular structure between an adjacent pair of data samples will simply be an average of each such data sample. Thus, the algorithms use graphical "fill in" techniques to depict a selected section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

Even with the most skilled physician, it is practically impossible to manually exercise sufficiently slow constant rate longitudinal translation of the ultrasound imaging device (which thereby provides for a precisely known separation distance between adjacent data samples). In addition, with manual translation, the physician must manipulate the translation device while observing the conventional two-dimensional sectional images. This division of the physician's attention and difficulty in providing a sufficiently slow constant translation rate can result in some diagnostic information being missed. To minimize the risk that diagnostic information is missed, it is necessary to lengthen the imaging scan time which may be stressful to the patient. Similarly, it is difficult for physicians to manually control the translational rate of atherectomy catheters and other interventional devices that are longitudinally advanced and retracted through blood vessel and other body lumens.

U.S. Pat. No. 5,485,486 discloses an ultrasound imaging transducer which is capable of being translated longitudinally within a section of a patient's vascular system at a precise constant rate through the use of a longitudinal translation assembly. The longitudinal translation assembly moves the entire rotary drive assembly to provide the desired longitudinal movement of the transducer. Such an ability enables a series of precisely separated data samples to be obtained thereby minimizing (if not eliminating) distorted and/or inaccurate reconstructions of the ultrasonically scanned vessel section (i.e., since a greater number of more closely spaced data samples can reliably be obtained). Also, such an assembly can be operated in a "hands-off" manner which allows the physician to devote his or her attention entirely to the real-time images with the assurance that all sections of the vessel are displayed. While such a longitudinal translation assembly can work well, it is relatively large, bulky and heavy; it is expensive; and it is cumbersome to set up, in part because the rotary drive and longitudinal translation assemblies are wrapped in separate sterile drapes or barriers (plastic bags) for sterility.

One of the disadvantages with some conventional pullback systems is separate modules are used to provide the rotational and translational movement. These modules require the use of sterile barriers about each. Also, some prior art pullback systems lack the capability to permit the user to manually translate the catheter core to preposition the operative element along the distal end of the catheter core.

SUMMARY OF THE INVENTION

The present invention is directed to a driveable catheter system which requires only one sterile drape to be used about a catheter drive unit. The catheter and the pull-back sled preferably include no electrical devices, such as motors, wires, batteries or electrical or electronic components, and can be made to be disposable after a single use. The invention is designed so that user set up and translational movement is simplified. Manual translational movement of the catheter core, with the operative element typically at is distal end, is easy and straightforward. The invention preferably provides translation displacement information on displays carried by both the catheter drive unit and the control unit. The catheter drive unit and the control unit are preferably coupled in a manner to permit two-way communication between the units thus permitting control signal inputs from the control unit as well as the catheter drive unit itself.

The driveable catheter system includes a driveable catheter assembly having a catheter drive unit movably mounted to a catheter drive sled. A catheter extends from the catheter drive unit. Typically the catheter includes an outer sheath, the proximal end of which if fixed in place by the sled, and a catheter core, which is translatable and rotatable within the catheter sheath by the catheter drive unit. A control unit is spaced apart from the catheter drive unit also and preferably provides power for the catheter drive unit. The control unit preferably provides inputs to and receives information from the catheter drive unit.

The sled preferably includes a base having a drive track and drive unit adapter configured for removably coupling the catheter drive unit to the sled base. The sled also preferably includes a sled drive train, one end of which has drive unit interface operably coupleable to the catheter drive unit. The other end of the sled drive train is coupled to the drive track. The drive unit interface preferably has a generally conical drive surface having a bag-piercing tip so that a sterile drape enclosing the catheter drive unit is automatically effectively pierced at the drive unit interface when the catheter drive unit is mounted to the drive unit adapter.

The catheter drive unit preferably includes a housing, a catheter core rotator within the housing and drive unit translator within the housing. The drive unit translator preferably includes a translator drive motor, a translator drive train operably coupling the translator drive motor to a translator drive output. The translator drive output is engageable with the preferably generally conical drive unit interface. The translator drive train preferably includes a user operable clutch for selectively decoupling the translator drive motor from the translator drive output. A translation displacement sensor is preferably located along the translator drive train between the clutch and the translator drive output so that actuating the clutch and manually moving the catheter drive unit along the sled continues to provide accurate translational location information for the user.

Translation displacement information is preferably provided on a display mounted to the catheter drive unit as well as on a display of the control unit. The catheter drive unit preferably includes a display reset button, a rotator drive ON/OFF button, and a translator drive ON/OFF button. The control unit preferably provides for rotator drive on/off input, translator drive on/off input, rotation speed input and translation speed input. The catheter unit drive and the control unit are coupled through a two-way communication link which permits control information to be provided to the catheter drive unit from the catheter drive unit and from the control unit; appropriate communication lines are used to permit operational information and data to be provided by the catheter drive unit to the control unit.

Other features and advantages of the invention will appear from the following description in which the preferred embodiment has been set forth in detail in conjunction with the accompanying drawings.

DESCRIPTION OF THE SPECIFIC EMBODIMENTS

Figure 1:
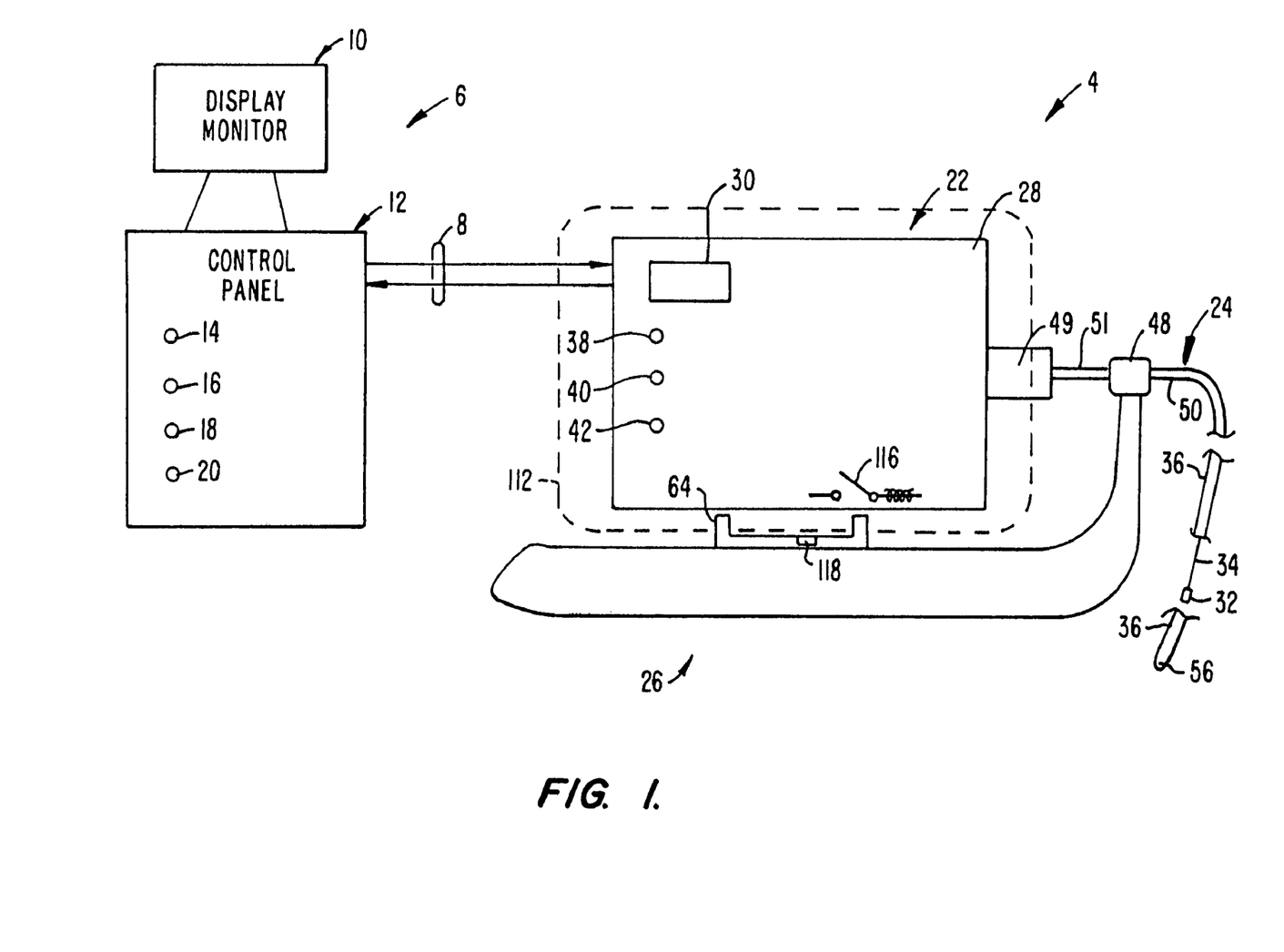
FIG. 1 is an overall system schematic diagram of a driveable catheter system made according to the invention.

FIG. 1 schematically illustrates a driveable catheter system 2 made according to the invention. System 2 includes broadly a driveable catheter assembly 4 operably coupled to a control unit 6 through a two-way data and communication link 8. One such two-way communication link includes an RS232 communication link which permits information and data from catheter assembly 4 to be directed to control unit 6 and permits instructions and control signals to be provided to driveable catheter assembly 4 from control unit 6.

Control unit 6 includes a display monitor 10 providing display of translation displacement information as well as other information. Control unit 6 also includes a control panel 12 which may include, for example, an alphanumeric keyboard, dedicated input buttons or a combination thereof. Other type of inputs including voice command input or a touch screen type of input can also be provided by control unit 6. In particular, control panel 12 provides for rotator drive on/off input 14, translator drive on/off input 16, rotation speed input 18 and translation speed input 20.

Figure 1A:
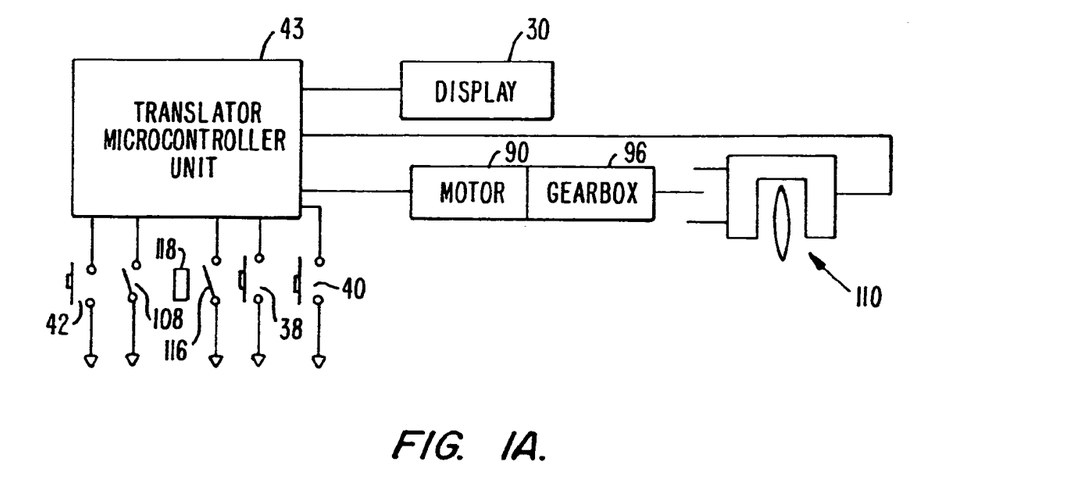
FIG. 1A is a simplified schematic representation of various components relating to translation of the catheter core of FIG. 1.

Driveable catheter assembly 4 includes broadly a catheter drive unit 22, a catheter 24 mounted to and extending from unit 22, and a catheter drive sled 26 engaging unit 22 and catheter 24. Catheter 24 includes a catheter core 34, with an operative element 32 (typically an ultrasonic transducer) at its distal end, housed within a catheter sheath 36. Catheter drive unit 22 includes a housing 28 to which an LCD translation displacement display 30 is mounted. Display 30 provides the user with translation displacement information relating to the translational (that is, longitudinal or axial) position of operative element 32. Catheter core 34 is rotatable and translatable (longitudinally slidable) within sheath 36 of catheter 24. A display reset button 38, used to reset translation displacement display 30 back to zero, is carried by housing 28. A rotator drive ON/OFF button 40 and translator drive ON/OFF button 42 are also carried by housing 28. This permits the user to start and stop both rotary and translational movement of catheter core 34 from both control unit 6 and catheter drive unit 22. FIG. 1A illustrates, in schematic form, various components relating to the translation of catheter core 34 coupled to a translator microcontroller unit 43, unit 43 being located within drive unit 22.

Figure 2:
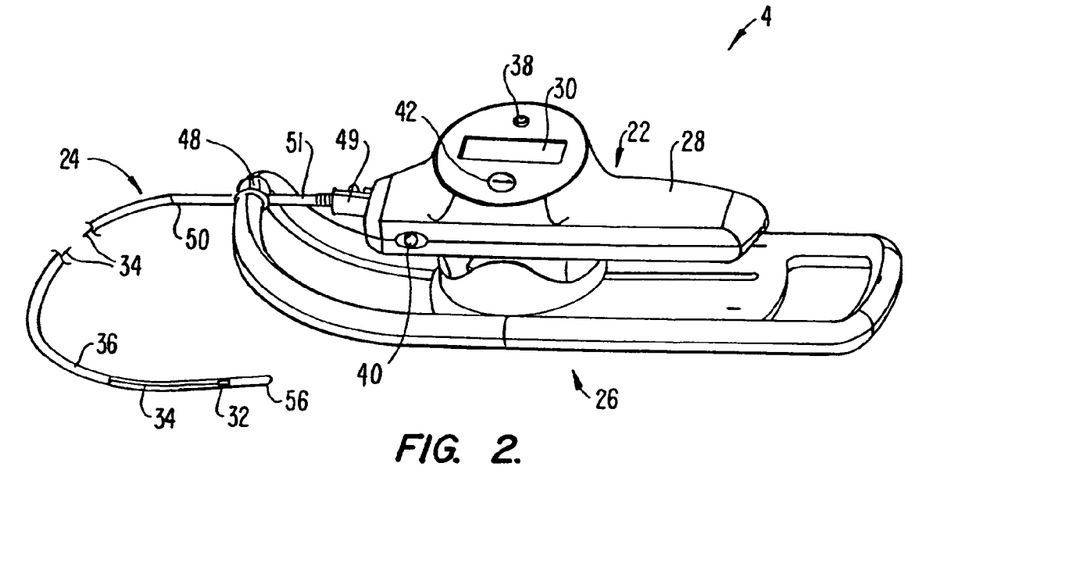
FIG. 2 is a perspective view of the driveable catheter assembly of FIG. 1 including the catheter drive unit, the catheter drive sled and the catheter.
Figure 3:
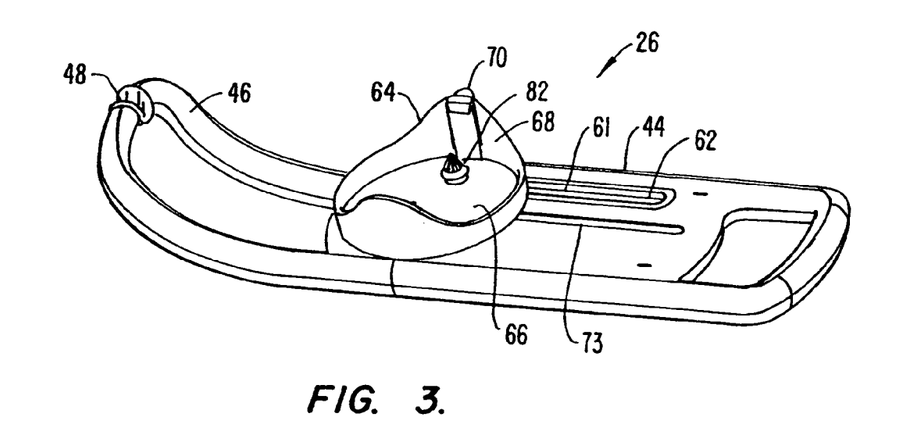
FIG. 3 is a perspective view the catheter drive sled of FIG. 2.

Turning now also to FIGS. 2 and 3, the components of driveable catheter assembly 4 will be discussed. Catheter drive sled 26 includes a sled body 44 having an upwardly extending, generally U-shaped nose portion 46. Nose portion 46 includes a sheath-engaging clip 48 used to anchor the proximal end 50 of sheath 36 to sled body 44. Sheath 36 includes a hub 49 which secures a telescoping portion 51 of sheath 36 to housing 28 of unit 22. Telescoping portion 51 has a smaller diameter and slides within proximal end 50 of sheath 36.

Figure 1B:
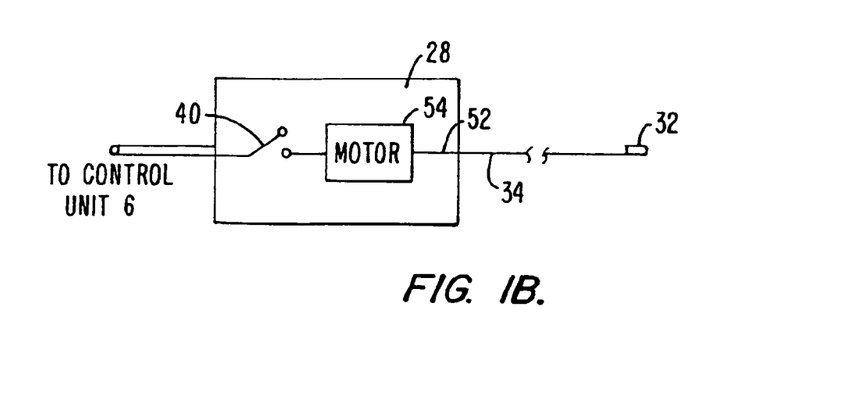
FIG. 1B is a simplified schematic diagram of rotary drive components of the catheter drive unit of FIG. 1.

The proximal end 52 of catheter core 34 is connected to and is rotated by a rotator drive motor 54, see FIG. 1B, carried within housing 28. Rotator drive motor 54 is fixed relative to housing 28 so that the translational movement of housing 28 causes corresponding translational movement of catheter core 34 within sheath 36 thus moving the operative element 32 towards and away from the distal end 56 of sheath 36.

Figure 4:
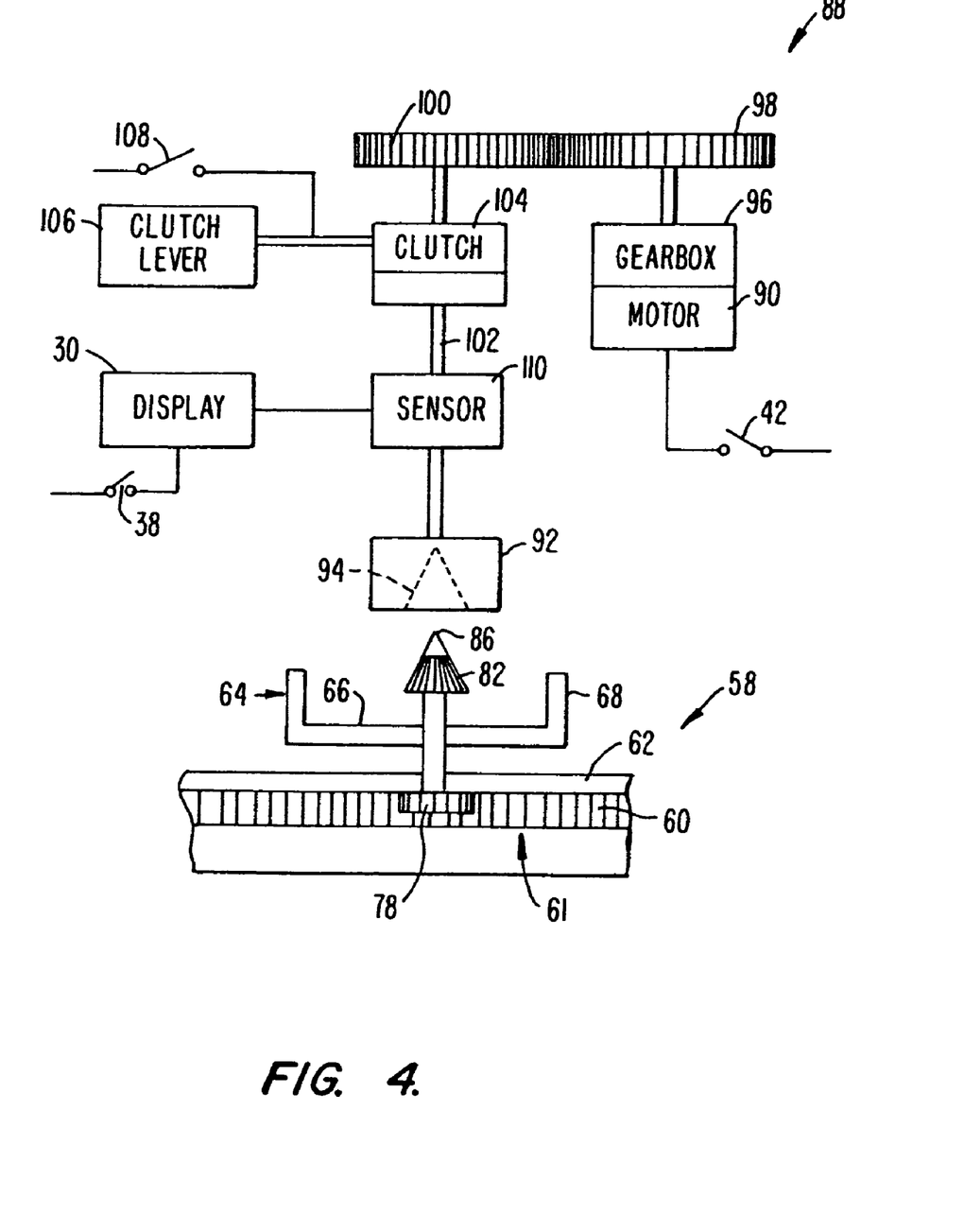
FIG. 4 is a schematic illustration of the translational drive components of the catheter drive unit and sled of FIG. 1.

FIG. 4 schematically illustrates the translational drive components of catheter drive unit 22 and sled 26. Sled 26 includes a sled drive train 58. Drive train 58 includes a rack gear 60; rack gear 60 defines a drive track 61 adjacent to and below a longitudinal slot 62 formed in sled body 44. See FIG. 3. Catheter drive sled 26 also includes a cup-like drive unit adapter 64 including a generally flat base 66 and an upstanding side wall 68. Side wall 68 includes a latch 70 used to automatically secure catheter drive unit 22 to catheter drive sled 26 when unit 22 is fully mounted to sled 26. To remove catheter drive unit 22 from sled 26, the user must manually disengage latch 70 from housing 28 of unit 22.

Figure 4A:
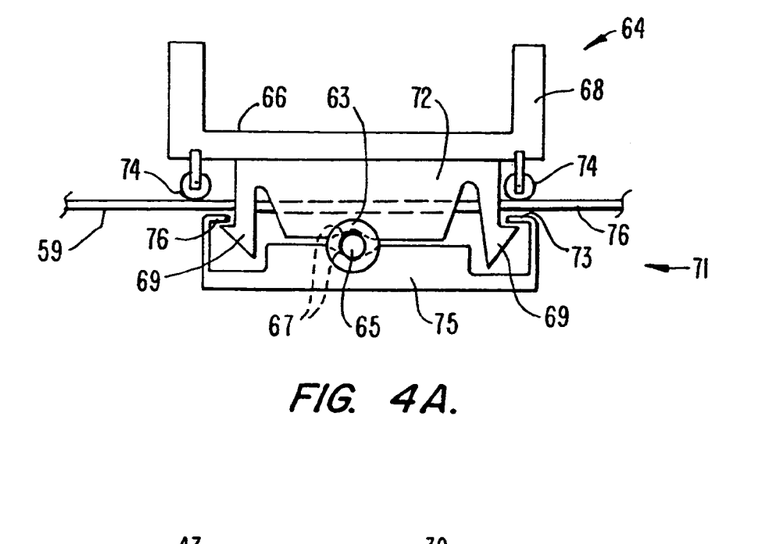
FIG. 4A is a simplified side view of the rolling support assembly for the adapter of FIG. 3.

Adapter 64 is mounted for longitudinal movement along sled body 44 by an adapter rolling support assembly 71 as shown in FIG. 4A. Assembly 71 includes a keel 72 fastened to and extending downwardly from base 66 of adapter 64. Keel 72 is relatively flat and thin to pass through a keel slot 73, seen also in FIG. 3, formed in sled body 44 parallel to slot 62. Adapter 64 is supported on sled body 44 by wheels 74. Keel 72 is secured to sled body 44 by a keel clip 75. Clip 75 has a pair of inwardly extending lips 76 which engage spring arms 69 of keel 72. Keel 72 and clip 75 have opposed V-shaped recesses 67 which capture an axle 65 therebetween. The axle has a support wheel 63 on either end which lie near keel 72 and clip 75 and rest against the inside wall 59 of sled body 44 on either side of slot 73.

Figure 5:
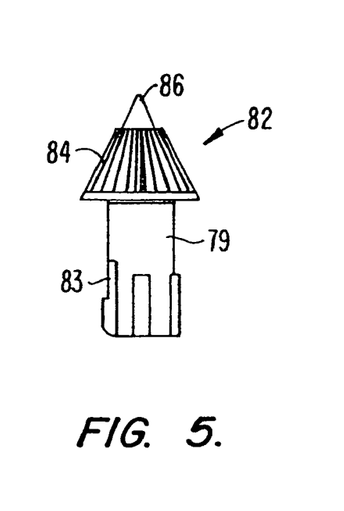
FIG. 5 is an enlarged side view of the drive unit interface of FIGS. 3 and 4.
Figure 5A:
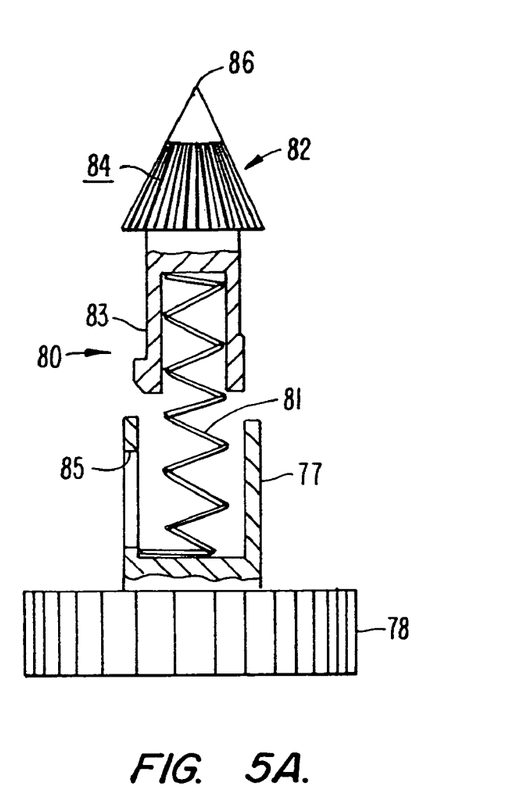
FIG. 5A is a simplified, exploded view of that portion of the sled drive train of FIG. 4 from the pinion gear to the drive unit interface.
Figure 6:
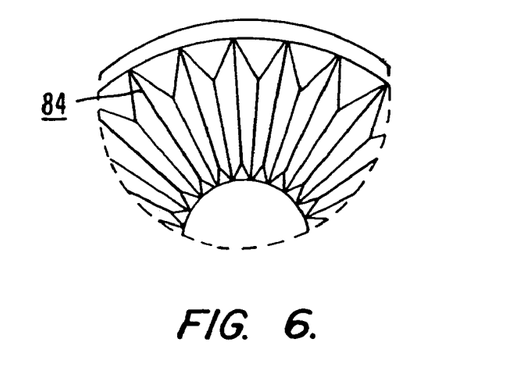
FIG. 6 is an enlarge partial top view illustrating the serrated nature of the conical drive surface of the drive unit interface of FIG. 5.

Sled drive train 58 includes a pinion gear 78 mounted to the lower end of a two-part, extendable drive shaft 80. See FIG. 5A. The upper end 79, see FIG. 5, of shaft 80 supports a drive unit interface 82 mounted thereon. Shaft 80 also includes an internal compression spring 81 which biases interface 82 upwardly; the upward movement of upper end 79 is limited by the engagement of a snap finger 83 of upper end 79 with an appropriately positioned surface 85 of lower end 77. Drive unit interface 82 is shown in more detail in FIGS. 5 and 6. Interface 82 includes a serrated, generally conical drive surface 84 and a sterile drape-piercing tip 86.

FIG. 4 also illustrates, in simplified form, a translator drive train 88 extending from a translator drive motor 90 to a translator drive output 92. Translator drive output 92 has a conical drive surface 94 sized for complementary mating engagement with conical surface 84 of drive unit interface 82. Motor 90 is coupled to a gear box 96 which drives a pair of pinion gears 98, 100.

Pinion gear 100 drives output 92 through a shaft 102. A clutch 104 is positioned along shaft 102 for the purposes to be discussed below. Clutch 104 is operated by a manual clutch lever 106; actuation of manual clutch lever 106 opens clutch 104 and causes a clutch switch 108 to open which turns off translator drive motor 90. When clutch 104 is disengaged, catheter drive unit 22 can be moved along drive track 61 while maintaining engagement of interface 82 and drive output 92. The translational position of catheter drive unit 22 (and more importantly of operative element 32) is provided by a translation displacement sensor 110 positioned between clutch 104 and output 92. Positioning sensor 110 between clutch 104 and output 92 ensures that translation displacement information is provided to display 30 and display monitor 10 regardless whether drive unit 22 has been moved by translator drive motor 90 or manually after disengagement of clutch 104.

In use, a catheter drive unit 22 and an appropriate catheter 24 are chosen. Catheter drive unit 22, which is preferably reusable, will typically be provided within a sterile bag or other sterile drape 112 illustrated in dashed lines in FIG. 1. Sterile bag 112 is a flexible, drapeable material, typically 2 mil polypropylene, as is conventional. Appropriate connections with two-way data and communication link 8 are made by a cable passing out of bag 112. Also, the hub 49 of catheter 24 is mounted to catheter drive unit 22 by passing through a hole in bag 112. (Sterile bag 112 is not shown in FIG. 2 for clarity of illustration.) Assembly 4 is then mounted to sled 26 as shown in FIG. 2. Catheter 24 and sled 26 are each provided in a sterile condition. Drive unit interface 82 and output 92 engage one another with the bag-piercing tip 86 of conical interface 82 effectively piercing bag 112. By effectively piercing it is meant that drive unit interface 82 can actually pierce and create a hole in the bag, or the bag can be captured between surfaces 84 and 94 (with or without a partial hole); in either case spring 81 creates sufficient force to create the desired mechanical engagement between elements 82 and 92.

The proper mechanical engagement is maintained by engagement of latch 70 with housing 28. The proper engagement is also aided by vertically spring loading one or both of interface 82 and output 92. In the preferred embodiment, surfaces 84, 94 are generally straight-sided conical surfaces. Other generally conical interfaces having convex or concave surfaces may be used. Generally conical surfaces include surfaces which are not truly conical but are shaped to help ensure proper registration of the elements and effective piercing of the sterility bag 112. Generally conical thus includes spherical surfaces, oval surfaces, stepped surfaces and other surface shapes which generally taper inwardly and provide the desired registration and drive functions.

Mounting unit 22 to sled 26 also includes clipping proximal end 50 of sheath 36 to clip 48 at nose portion 46 of sled body 44 while telescoping portion 51, extending from hub 49, is free to telescope into and out of proximal end 50. There is a sliding seal between end 50 and portion 51 to prevent contamination of catheter core 34. Translational movement of unit 22 along drive track 61 causes translation of catheter core 34 but not of sheath 36; this causes the back and forth movement of operative element 32 at the distal end of catheter core 34 relative to distal end 56 of sheath 36.

Once unit 22 and sled 26 are properly secured to one another, clutch lever 106 can be moved to permit the user to properly locate unit 22 along drive track 61. At this time display reset button 38 can be pressed to zero-out the translation displacement information at displays 10, 30.

Distal end 56 of catheter 24 is positioned to an appropriate location within the patient. Rotational and translational speeds are determined and programmed at inputs 18, 20. Instead of inputting separate parameters, control unit 6 could be set up so that, if desired, once a procedure is chosen, the procedure dictates, or suggests, the various operational parameters to be used.

Mounting assembly 4 to sled 26 also causes magnetic switch 116 to be actuated, typically closed, by the presence of a magnet 118 within drive unit adapter 64. See FIG. 1. In lieu of a magnetic switch, other types of proximity switches could be used. In addition, magnetic switch 116 could be replaced by a switch which would automatically be actuated only when assembly 4 is fully mounted to sled 26. For example, a switch could be within housing 28 of unit 22 and actuated when latch 70 engages housing 28. With magnetic switch off, that is with catheter drive unit 22 not mounted to sled 26, display 30, sensor 110 and motor 90 are all off. Once unit 22 is mounted to sled 26, display 30 and sensor 110 are turned on while motor 90 remains off. Rotary drive motor 54 is actuated by using button 40 or input 14 which causes catheter core 34, and thus operative element 32, to rotate. Upon pressing of translator drive ON/OFF button 42 or instituting translational movement through translator drive on/off input 16, motor 90 is turned on and the changing position of operative element 32 is indicated at displays 10, 30. If the user actuates manual clutch lever 106, this not only disconnects motor 90 from output 92, it actuates switch 108 which also causes motor 90 to turn off.

The invention is typically used in a pullback mode. If desired, the invention could be used to push operative element 32 towards distal end 56 of sheath 36. To prevent injury to the patient or damage to the unit, motor 90 will be turned off when catheter drive unit 22 reaches the end of travel along drive track 61 as sensed by a current sensor monitoring the current to motor 90. Motor 90 will also be automatically turned off if an obstruction is sensed, the obstruction preventing or hindering movement of unit 22 along drive track 61.

Modification and variation can be made to the enclosed embodiment without departing from the subject of the invention as defined in the following claims. For example, according to certain aspects of the invention sled 26 could include a battery to power motor 90; in this case interface 82 and output 92 could include both mechanical and electrical connections or separate electrical connectors could be included with unit 22 and sled 26. Sled 26 could be made of sterilizable materials so that the sled could be used more than once by users having the appropriate sterilization facilities.

Any and all patents, patent applications and publications referred to above are incorporated by reference.

What is claimed is:

1. A catheter drive system comprising a catheter drive sled and a catheter drive unit removably mountable to the catheter drive sled, the catheter drive sled comprising:
   a sled body defining a keel slot and a keel clip that is disposed in the keel slot and that is movable along an axis of the keel slot;
   a drive unit adapter mounted to the sled body, the drive unit adapter comprising a keel that extends into the keel slot and that couples to the movable keel clip; and
   a sled drive train disposed on the sled body, the sled drive train comprising a drive track and a drive unit interface coupled to the drive track via a drive shaft, the drive unit interface and the drive unit adapter configured and arranged for removably mounting a catheter drive unit to the sled body, wherein the drive shaft of the sled drive train extends through the drive unit adapter;
   wherein the drive unit interface comprises a serrated surface with a sterile pointed tip.

2. The catheter drive system according to claim 1 wherein the sled body comprises a raised nose portion.

3. The catheter drive system according to claim 2 wherein the nose portion comprises a catheter sheath engagement member.

4. The catheter drive system according to claim 1 wherein the drive track comprises a rack having a plurality of teeth.

5. The catheter drive system according to claim 1 wherein the catheter drive sled is a single use, disposable sled.

6. The catheter drive system according to claim 5 wherein the catheter drive sled is free from any electrical device.

7. The catheter drive system of claim 1, wherein the catheter drive unit comprises:
   a housing;
   a catheter core rotator within the housing;
   a drive unit translator within the housing, the drive unit translator comprising:
      a translator drive motor;
      a translator drive output configured and arranged to removably couple to the drive sled;
      a translator drive train operably coupling the translator drive motor and the translator drive output, wherein the translator drive train includes means to selectively decouple the translator motor from the translator drive output; and
      a translation displacement sensor located along the translator drive train between a clutch and the translator drive output, and a translator drive ON/OFF button operably coupled to the drive unit translator, wherein the translator drive ON/OFF button is mounted to the housing, and further comprising a clutch lever to operate the clutch.

8. the catheter drive system according to claim 7 wherein the catheter drive unit further comprises a rotator drive ON/OFF button operably coupled to the catheter core rotator, wherein the rotator drive ON/OFF button is mounted to the housing.

9. The catheter drive system according to claim 7 wherein the catheter drive unit further comprises a translation displacement display mounted to the housing and operably coupled to the translation displacement sensor.

10. The catheter drive system according to claim 9 wherein the catheter drive unit further comprises a position reset button operably coupled to the translation displacement display.

11. The catheter drive system according to claim 9 wherein the catheter drive unit further comprises a position-sensitive switch, actuatable when the catheter drive unit is mounted to and dismounted from a catheter drive sled, operably coupled to the translator drive motor and the translation displacement display.

12. The catheter drive system according to claim 11 wherein the position-sensitive switch comprises a magnetic switch.

13. The catheter drive system according to claim 7 wherein the catheter drive unit is adapted to be housed within a pierceable sterile drape and the translator drive output comprises a generally conical drive surface.

14. The catheter drive system according to claim 13 wherein the generally conical drive surface defines a generally conical open region.

15. The catheter drive system of claim 1 further comprising:
- a catheter comprising a rotatable and translatable catheter core operably coupled to and extending from the catheter drive unit;
- the catheter drive unit comprising
  - a means for translating the catheter drive unit and the catheter core therewith relative to the sled;
  - a means for rotating the catheter core;
  - a proximity switch operably coupled to at least one of the means for translating the catheter drive unit or the means for rotating the catheter core; and
  - a means for activating the proximity switch when the catheter drive unit is mounted to the sled.

16. A method for setting up the catheter drive system of claim 1 comprising:
- providing the catheter drive unit with a catheter extending therefrom, the catheter comprising a rotatable and translatable catheter core, and means for rotating and translating the core the catheter drive unit being enclosed within a drapeable barrier;
- mounting the catheter drive unit to the catheter drive sled such that the drive unit interface of the catheter drive sled mates with the means for rotating and translating the core, wherein the catheter drive unit comprises a catheter core rotator; and
- said mounting step comprising effectively piercing the drapeable barrier by the engagement of the means for rotating and translating the core and the drive unit interface.

17. The method according to claim 16 wherein the selecting step is carried out with the serrated surface of the drive unit interface having a generally conical drive surface.

18. The method according to claim 17 wherein said selecting step is carried out with the sterile pointed tip comprising a barrier-piercing tip.

19. A method for setting up and using the catheter drive system of claim 1 comprising:
- selecting the catheter drive unit having a translator drive output, the catheter drive unit being enclosed within a removable drapeable barrier; and
- mounting the catheter drive unit to the catheter drive sled such that the drive unit interface of the catheter drive sled mates with the translator drive output, wherein the catheter drive unit comprises a catheter core rotator;
- said mounting step comprising effectively piercing the drapeable barrier by the engagement of the translator drive output and the drive unit interface.

20. The method according to claim 19 further comprising viewing translation displacement information from displays at the catheter drive unit and the control unit.

21. The catheter drive system according to claim 1 wherein the drive unit adapter comprises at least one wheel that rolls along a surface of the sled body.

22. The catheter drive system according to claim 1 wherein the drive track and the keel slot extend parallel to one another along a surface of the sled body.

* * * * *